United States Patent [19]
Noddin et al.

[11] Patent Number: 4,963,313
[45] Date of Patent: Oct. 16, 1990

[54] BALLOON CATHETER

[75] Inventors: Richard A. Noddin, Holliston; Arthur R. Madenjian, Waltham; Ralph J. Barry, Jr., Hudson, all of Mass.

[73] Assignee: Boston Scientific Corporation, Watertown, Mass.

[21] Appl. No.: 126,769

[22] Filed: Nov. 30, 1987

[51] Int. Cl.$^5$ .................. B29D 22/00; B29C 45/00
[52] U.S. Cl. .................. 264/573; 264/512; 604/96; 606/194
[58] Field of Search .................. 604/96–103; 264/291, 292, 570, 573, 512; 606/192–194

[56] References Cited

U.S. PATENT DOCUMENTS

| | | | |
|---|---|---|---|
| 3,865,666 | 2/1975 | Shoney | 156/245 |
| 3,950,468 | 4/1976 | Rainville | 264/97 |
| 4,256,789 | 3/1981 | Suzuki et al. | 428/35 |
| 4,323,071 | 4/1982 | Simpson et al. | |
| 4,411,055 | 10/1983 | Simpson et al. | 29/447 |
| 4,422,447 | 12/1983 | Schiff | 128/1 D |
| 4,490,421 | 12/1984 | Levy | 428/35 |
| 4,587,975 | 5/1986 | Salo et al. | |
| 4,646,719 | 3/1987 | Neuman et al. | |

OTHER PUBLICATIONS

EP O 1359 990—"Balloon and Manufacture Thereof", E. I. Du Pont de Nemours and Company, Apr. 3, 1985, Bulletin 85/14.
Ver Hage, Glenn R. et al., "Injection Blow Molding Parts with Openings at Both Ends", Harper Handbook of Plastics & Elastomers.
Shriver C. et al., "How to Reheat Blow Mold PET Soft-Drink Bottles", Plastic Technology, vol. 23, No. 11, pp. 91–93, Oct., 1977.
Miller B. H., "Reheat Blow Molding of Pet Bottles", Society of Plastic Engineers Technical Paper Annual Technical Conference, 1980.
EP. Publication No. 0,274,411, published Jul. 13, 1988 (Priority Claim U.S.S.N. 001,759, filed Jan. 9, 1987).

Primary Examiner—Stephen C. Pellegrino
Attorney, Agent, or Firm—Fish & Richardson

[57] ABSTRACT

An inflatable medical balloon is formed by fabricating a tubular preform having a tapered region at the end of the portion where the main body of the balloon will form to enable the corresponding transition section of the blown balloon to have a separately controllable thickness profile. The preferred method includes providing a tube of a selected resin of wall thickness and diameter suitable for being formed into a balloon, and selectively heating to drawing temperature a defined region of the tube at one or both ends of the portion of the tube from which the balloon is to be formed. Tension is applied in opposite directions to respective ends of the heated region to draw the region to a smaller diameter, thereby providing a preform having, at the end of the portion of the tube, a tapered, relatively small diameter region of material that has substantially no crystallization or molecular orientation. In preferred embodiments a tapered region is provided at both ends of the portion in which the main body of the balloon is to be formed. Thereafter the tubular preform is heated to blowing temperature and, while heated, a balloon is formed by drawing and blowing the preform including the tapered regions. The balloon is mounted to form a balloon catheter device. A dilatation balloon catheter, is also described having wall thickness in the transition region less than 0.001 inch.

11 Claims, 4 Drawing Sheets

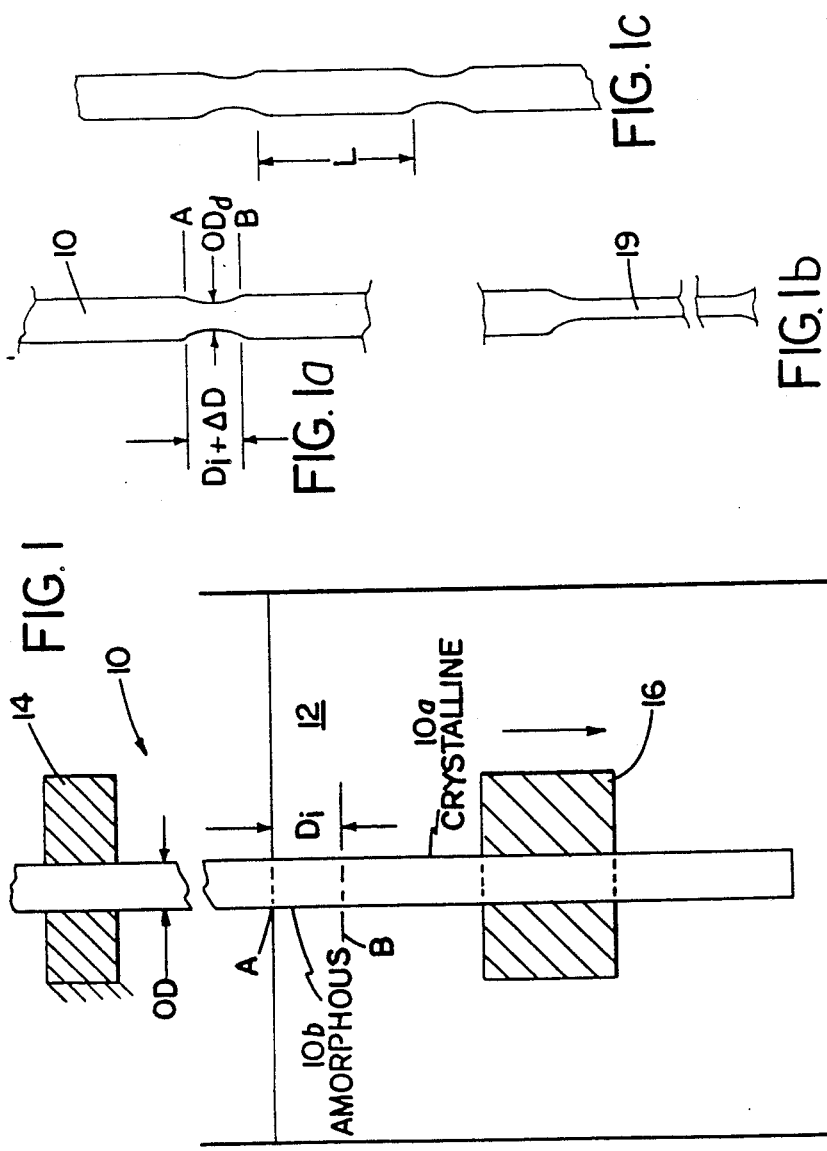

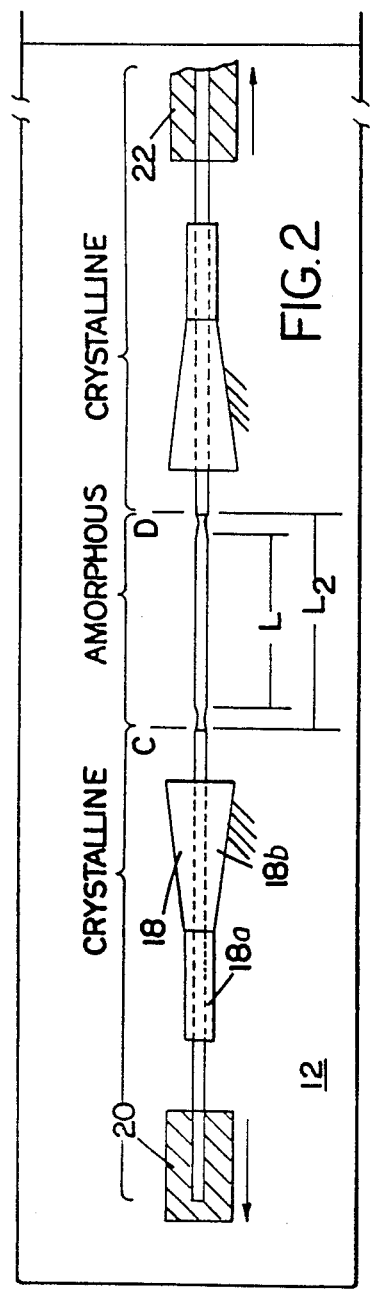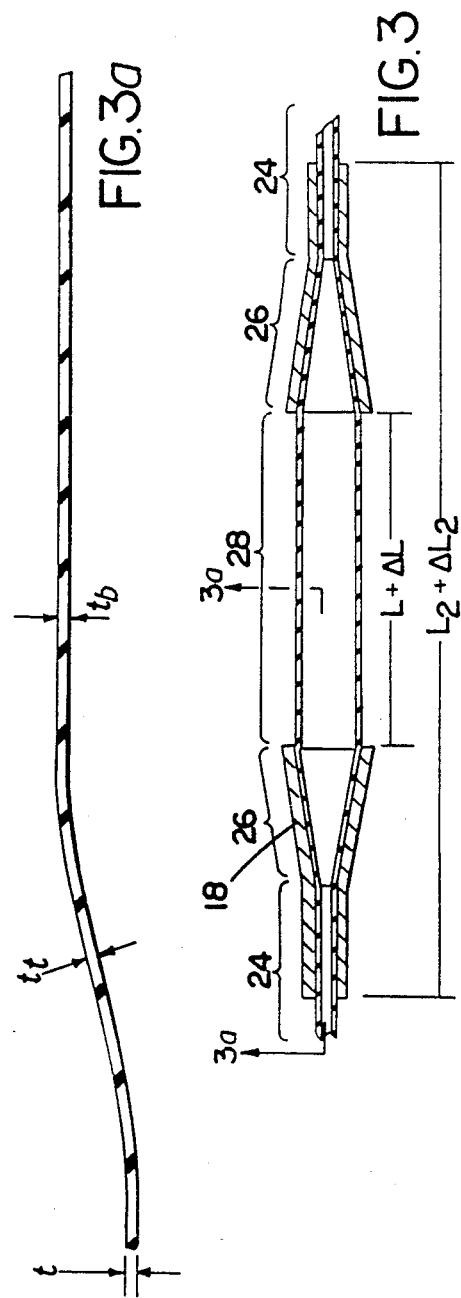

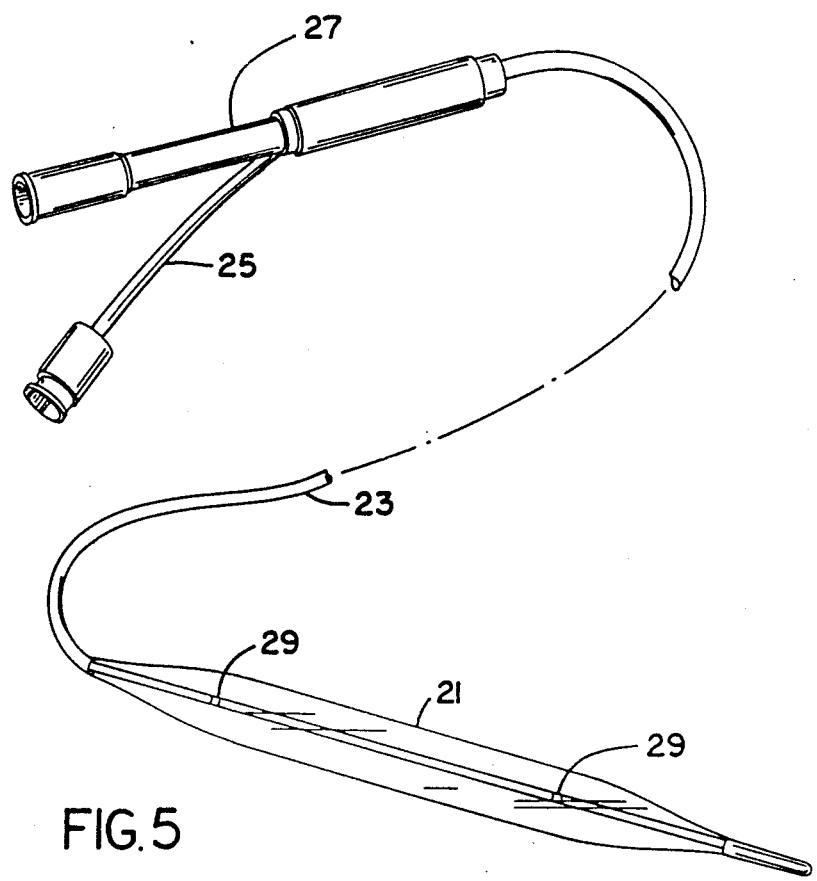

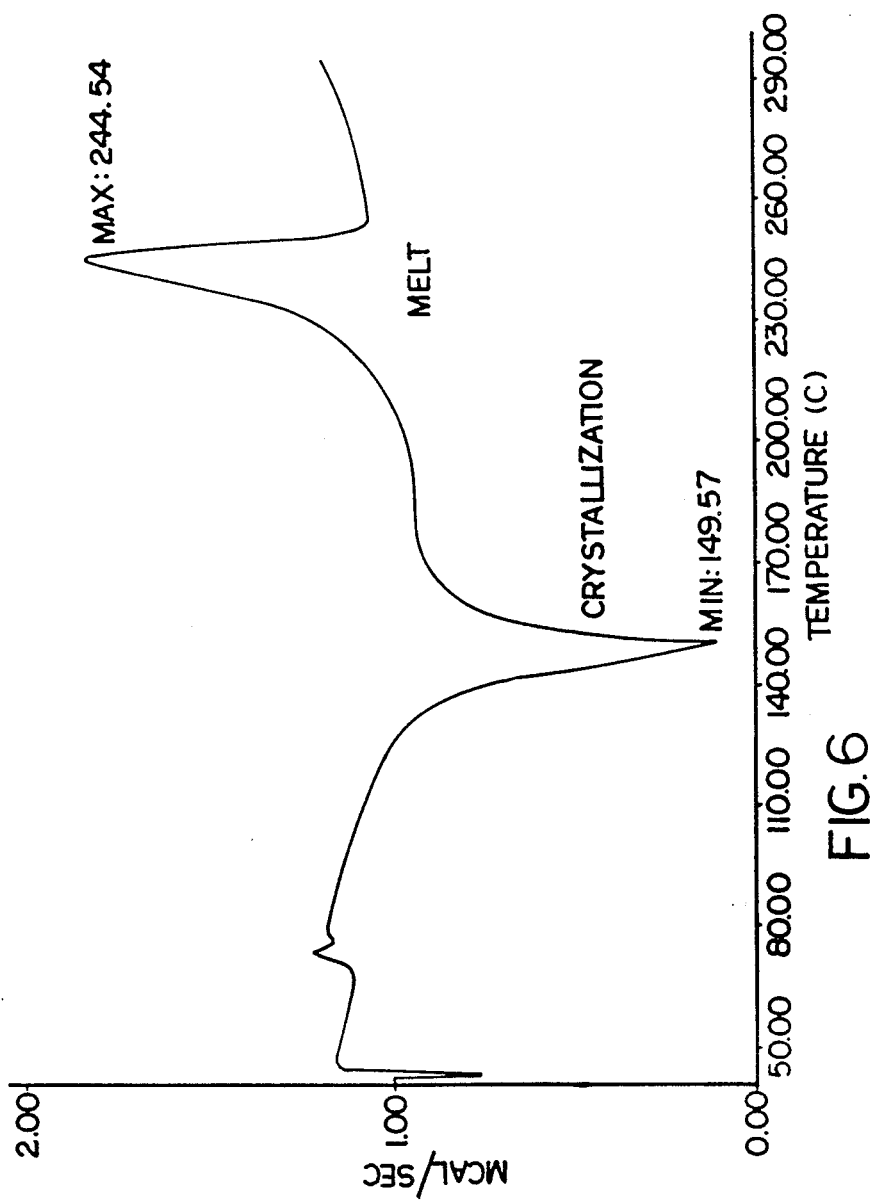

BALLOON CATHETER

BACKGROUND OF THE INVENTION

The invention relates to medical balloons and especially to angioplasty dilatation balloon catheters.

Such balloons are intended to be collapsed to small size about their long supporting devices. In the case, e.g., of angioplasty balloon catheters, the small size is necessary to enable advance of the catheter through narrow and curved blood vessels into the region of stenosis where the balloon is to be inflated. After use, the balloon must be deflated and withdrawn. It is important in such movements not to damage the vessel walls or other delicate tissue of the body.

The process of making such balloons usually starts with an extruded cylindrical tube of a given diameter and wall thickness. The tube, in its amorphous state, is heated to blowing temperature and inflated and drawn longitudinally. Thus a tube of amorphous polyethylene terephthalate can be drawn and expanded to achieve a wall thickness of less than 0.001 inch in the main body of the balloon with wall thicknesses that increase in the tapered proximal and distal transition regions.

Whereas such balloons have been found to be quite useful, especially when high strength resins are employed to provide correspondingly high pressures of inflation, there have been disadvantages attributable to the thickness of the balloon material in the transition regions.

During folding of the balloon and wrapping it around the catheter shaft to make it small size for insertion, protruding bumps or distortions occur at the ends of the balloon. Because of the thickness of the material at these regions, these distortions can be relatively stiff and sharp and can cause trauma to the arteries or other passages through which the balloon is passed.

One area in which improvement is particularly needed in this regard is that of large diameter, high pressure angioplasty balloon catheters, i.e., balloon catheters in which the diameter of the main body of the balloon, when inflated, is between about 5 to 12 millimeters.

Also, known techniques have made it difficult to achieve balloon catheters for other applications, for instance, balloon catheters that require elongated sleeves to fit tightly over very small catheters.

SUMMARY OF THE INVENTION

According to one aspect of the invention, a method of forming an inflatable medical balloon and a product made according to that method is characterized by the steps of providing a tube of a selected resin of wall thickness and diameter suitable for being formed into a balloon, selectively heating to drawing temperature a defined region of the tube at one or both ends of the portion of the tube from which the balloon is to be formed, applying tension in opposite directions to respective ends of the heated region to draw the region to a smaller diameter, thereby providing a preform having, at one or both ends of the portion of tube, a tapered, relatively small diameter region comprised of material that has substantially no crystallization or molecular orientation, thereafter heating the tubular preform to blowing temperature and, while heated, forming a balloon by drawing and blowing the preform including the tapered regions and mounting the balloon to form a balloon catheter device, the step of preforming the tapered end regions enabling the corresponding sections of the blown balloon to have a separately controllable thickness profile.

In preferred embodiments of this aspect of the invention, the drawing temperature is above the glass transition temperature and below crystallization temperature such that substantially no crystallization or molecular orientation occurs; the drawing temperature is near or above the melt temperature of the resin and after drawing, the balloon is rapidly quenched; the blowing temperature is approximately the glass transition temperature or above, and substantially below the crystallization temperature of the resin; for biaxially orienting the balloon, the blowing temperature is below the drawing temperature, in the region of the glass transition temperature of the resin; the resin is amorphous polyethylene terephthalate, the drawing temperature is between about 105 and 130 degrees centigrade and the blowing temperature is between about 85 and 115 degrees centigrade; the drawing to form the preform and the step of drawing and blowing the preform are so related that the wall thickness of the main body of the balloon and the wall thickness of a tapered transition section of the balloon are of substantially equal value or the wall of the transition section is thinner; the heating of the defined region is performed in such a manner that the portion of the tube from which the main body of the balloon is to be formed is not substantially heated.

According to another aspect of the invention, a dilatation balloon catheter for angioplasty is provided comprising an elongated, small diameter catheter adapted to be passed through the vascular system of the body to a point of stenotic occlusion of a blood vessel, an inflatable dilatation balloon secured about the catheter, adapted to be inflated at the point of occlusion to enlarge the blood vessel and relieve the restriction to blood flow, the balloon comprising a main body section of full diameter and at least one tapering transition section at one end of the main body section, and means to inflate and deflate the balloon, the catheter being characterized in that the balloon is the product of the process of blowing and drawing a preformed tubular member having a tapered contour in the region corresponding to the transition section of the blown balloon.

In preferred embodiments of this aspect of the invention the preformed tubular member is the product of heating and drawing a defined region of an extruded tube of originally constant diameter and wall thickness; the main body section and the tapering transition section of the balloon have substantially the same wall thickness or the transition section is thinner; the main body of the balloon has an inflated diameter of 5 mm or larger; and the resin from which the balloon is formed is polyethylene terephthalate.

DESCRIPTION OF THE PREFERRED EMBODIMENT

We first briefly describe the drawings.

FIG. 1 is a diagramatic view of an extrusion-formed tubular element of a selected resin material being heated and drawn as a step of the present invention. FIG. 1a is a diagramatic view of a drawn section of the tubular element. FIG. 1b is an alternate view similar to 1a of another form with a more elongated necked-down region than shown in FIG. 1a. FIG. 1c is a view on a smaller scale showing the entire preform with two necked down regions separated by a distance L.

FIG. 2 is a diagramatic view of the preform of FIG. 1c in a position ready to be blown into a balloon. FIG. 3 is a view similar to FIG. 2 but in cross-section showing the formed balloon. FIG. 3a is a cross-section of the wall of the balloon of FIG. 3 showing the generally uniform wall thickness achievable along the length of the tube. FIG. 4 is a side view of a finished balloon produced according to the invention. FIG. 5 is a similar view of an angioplasty balloon catheter according to the invention. FIG. 6 is a thermal analysis curve of PET resin.

DETAILED DESCRIPTION OF PREFERRED EMBODIMENT

Referring to FIG. 1, a tube suitable for blowing a medical balloon of 8 mm diameter is provided, comprised of a nondistendable resin, Goodyear's Clear Tuf 8006, polyethylene terephthalate, having an outer diameter of 0.066 inches and a wall thickness of 0.011 inches. A portion 10a of the tube, up to line B has been crystalized to render it dimensionally stable under heated conditions. The portion thus stabilized can not be appreciably inflated or drawn. The tube 10 is immersed in a heated bath 12 of glycerine at a drawing temperature selected from the range of about 105 to 130 degrees centigrade, e.g., 120 degrees centigrade. The crystalized region is fully immersed together with a short portion, $D_i$, e.g., 3 mm, of the amorphous portion 10b of the tube. The portion of the tube out of the bath is gripped by a fixed clamp 14, and the crystallized portion of the tube submerged in the bath is gripped by a moveable clamp 16. After a suitable duration of immersion, to ensure that the resin reaches the temperature of the bath, clamp 16 is moved downwardly a predetermined distance, e.g., 2 mm, at a draw rate in the range of about one inch to 0.1 inch per minute, e.g., 0.3 inch per minute, in the direction of the arrow, causing the heated amorphous portion of the tube to be drawn, the crystallized portion resisting such deformation. Referring to FIG. 1a, tube 10, in the region between A and B as shown in FIG. 1, is necked-down as a result of such drawing. The degree of necking and thinning of the walls obviously depends upon the conditions of drawing, e.g., the drawing rate, drawing temperature, length of the amorphous portion being drawn and the distance of draw, the values of which for any particular balloon can be determined by ready trial. In the preferred embodiment being described, the tube's outer diameter $OD_d$, is necked-down to 0.054 inch and the tube is lengthened 2 mm. In the alternative embodiment of FIG. 1b in which a longer portion of the amorphous tube has been immersed, the tube is drawn down to a constant diameter sleeve 19.

After the initial necking-down of the tube, the tube is reversed in the bath and the second necked-down portion is formed by the same procedure, at a point spaced along the amorphous tube a distance L, e.g., 0.57 inch, to provide a section of tube between the necked-down regions which will be drawn and blown in forming the main body of the balloon. This procedure can provide a preform in which the thickness of the wall of the tube in the region of the drawn-down deformation decreases with decrease in diameter.

After the preform is completed, it is submerged in a second bath of glycerine as shown in FIG. 2, this time arranged horizontally, and with the tube extending through two stationary constraining elements 18, the crystallized portions of the tube being grasped by clamps 20 and 22. The temperature of bath 12a is regulated to correspond to the desired blowing temperature, selected from the range of about 85 to 115 degrees centigrade, e.g., 90 degrees centigrade. Each constraining element 18 is comprised of a cylindrical portion 18a and a conical portion 18b, the wide ends of the conical portions being opposed to each other, arranged to define the shape of the tapered sections of the balloon.

As shown, the crystallized regions of the tube and at points C and D in the initial setup of FIG. 2. After the temperature of the tube has stabilized in bath 12a, the two clamps 20 and 22 are drawn apart, causing the tube to slide through the stationary constraining elements 18 as it is lengthened. Simultaneously, gas pressure is applied to the interior of the tube, causing it to expand. The region, L, of the tube expands without constraint until the molecules of the wall material in the balloon region become stabilized in a biaxially oriented condition. In its final form, the balloon reaches an OD of 8 mm and the length between the tapered sections increases to $L+\Delta L=1.51$ inches. The portions of the tube having the preformed tapers also expand until they are constrained to the shape of constraining element 18. The final balloon thickness profile is illustrated in FIG. 3a in which the thickness of the balloon $t_b$ is 0.0007 inches and the thickness $t_t$ of the tapered wall is substantially of the same value with variation less than about 0.0001 inch. The length of the amorphous region during the blow and draw step increases from $L_2=0.94$ inch to $L_2+\Delta L_2=2.70$ inch.

In another embodiment, in forming the preform, e.g., by drawing more on the defined region, and thus drawing the taper down further, it is possible to achieve in the blown balloon a wall thickness of the transition region that is less than that of the main body of the balloon.

After formation of the balloon, the balloon is cooled dried, the end portions are cut away, e.g., the portions extending outwardly from the smallest diameter of the necked down region, and the balloon 21 is assembled upon a suitable catheter 23 which has a balloon inflation lumen 25 for inflation of the balloon and a through lumen 27 for receiving a guidewire, see FIG. 5. Radiopaque markers 29 are provided on the catheter at the ends of the main body of the balloon 21. In this manner, a large balloon, e.g., of 8 mm diameter, capable of pressures of, e.g., 8 atmospheres can be obtained, having transition regions that are sufficiently thin to enable very successful dilatation.

A further advantage of the invention is obtained when making the larger balloon sizes for assembly on small catheters, for instance an 8 mm balloon on a 5 French catheter. To form such a balloon, it is advantageous to choose a starting tube of diameter greater than the outer diameter of the catheter on which the balloon is ultimately to be mounted. By use of the drawing steps to form the preform, it is readily possible, in the defined heated regions, to draw the diameter of these regions to a size corresponding to the size of the catheter.

In other embodiments the wall thickness of the tapered section can be increased or decreased according to the amount of draw performed during fabrication of the preform. In some embodiments the use of constraining elements in the end regions may be omitted and in other embodiments the entire preform may be confined in a mold for determining the final blown shape. The temperature in other embodiments may be outside of the preferred ranges mentioned, provided certain relationships are maintained as described in the summary of the invention, above, with reference to the thermal analysis curve for the respective resin; see the example for the preferred embodiment, FIG. 6.

For certain of the broader aspects of the invention, other forming techniques such as molding of a softened tube are possible for preparing the tapered preform.

What is claimed is:

1. A method of forming an inflatable medical balloon catheter device comprising
   (a) providing a tube of a selected resin of wall thickness and diameter suitable for being formed into a balloon, said tube having at least a first region crystallized to render it dimensionally stable under heated conditions,
   (b) selectively heating to drawing temperature a defined second region of said tube disposed at an end of the portion of the tube from which the balloon is to be formed, between said portion of tube and said first region,
   (c) applying tension in opposite directions to respective ends of said heated region to draw the second region to a smaller diameter, thereby providing a preform having, at the end of said portion of tube, a tapered, relatively small diameter region comprised of material that has substantially no crystallization or molecular orientation,
   (d) thereafter heating said tubular preform to blowing temperature and, while heated, forming a balloon by drawing and blowing said preform including said tapered region, and
   (e) mounting said balloon on a catheter to form a balloon catheter device,
       said step of preforming said tapered end region enabling the corresponding section of the blown balloon to have a separately controllable thickness profile.

2. A method of forming an inflatable medical balloon catheter device comprising
   (a) providing a tube of a selected resin of wall thickness and diameter suitable for being formed into a balloon, said tube having two, spaced apart first regions crystallized to render it stable under heated conditions,
   (b) selectively heating to drawing temperature two defined second regions of said tube disposed at the respective ends of the portion of the tube from which the balloon is to be formed, between the respective ends of said portion of tube and said second regions,
   (c) applying tension in opposite directions to respective ends of said heated regions to draw the second regions to smaller diameter, thereby providing a preform having, at the ends of said portion of tube, tapered, relatively small diameter regions comprised of material that has substantially no crystallization or molecular orientation,
   (d) thereafter heating said tubular preform to blowing temperature and, while heated, forming a balloon by drawing and blowing said preform including said tapered regions, and
   (e) mounting said balloons on a catheter to form a balloon catheter device,
       said step of preforming said tapered end regions enabling the corresponding sections of the blown balloon to have a separately controllable thickness profile.

3. The method of claim 1 or 2 wherein said drawing temperature is above the glass transition temperature and below crystallization temperature such that substantially no crystallization or molecular orientation occurs.

4. The method of claim 1 or 2 wherein said drawing temperature is near or above the melt temperature of said resin and after drawing, said preform is rapidly quenched.

5. The method of claim 1 or 2 wherein said blowing temperature is approximately the glass transition temperature or above, and substantially below the crystallization temperature of said resin.

6. The method of claim 5 wherein, for biaxially orienting the balloon, said blowing temperature is below the drawing temperature, in the region of the glass transition temperature of said resin.

7. The method of claim 1 or 2 wherein said resin is amorphous polyethylene terephthalate, said drawing temperature is between about 105 and 130 degrees centigrade and said blowing temperature is between about 85 and 115 degrees centigrade.

8. The method of claim 1 or 2 wherein said drawing to form said preform and said step of drawing and blowing said preform are so related that the wall thickness of the main body of the balloon and the wall thickness of a tapered end section of the balloon are of substantially equal value.

9. The method of claim 1 or 2 wherein said heating of said defined region is performed in such a manner that the portion of the tube from which the main body of the balloon is to be formed is not substantially heated.

10. A balloon product made according to the method of claim 1 or 2.

11. A balloon product made according to the method of claim 8.

* * * * *